United States Patent [19]

Teulon et al.

[11] 4,096,270

[45] Jun. 20, 1978

[54] 4-(2-CHLORO- OR METHYLTHIOPYRID-3-yl)-3,5-DICARBALKOXY-2,6-DIMETHYL-1,4-DIHYDROPYRIDINE

[75] Inventors: Jean-Marie Teulon, La Celle Saint-Cloud; Bernard Schweisguth, Meudon; Jean-Claude Cognacq, Bourg La Reine, all of France

[73] Assignee: Societe Anonyme Dite : Hexachimie, Rueil-Malmaison, France

[21] Appl. No.: 711,862

[22] Filed: Aug. 5, 1976

[30] Foreign Application Priority Data

Aug. 12, 1975 United Kingdom .............. 33501/75
Oct. 31, 1975 United Kingdom .............. 45188/75

[51] Int. Cl.$^2$ ................. C07D 213/55; A61K 31/455
[52] U.S. Cl. ............................ 424/266; 260/294.8 G; 260/295.5 R
[58] Field of Search ................ 260/295.5 R, 294.8 G; 424/266

[56] References Cited

U.S. PATENT DOCUMENTS 3,773,773  11/1973  Bossert .................... 260/295.5 R
3,799,934  3/1974   Meyer et al. ............. 260/295.5 R

*Primary Examiner*—Alan L. Rotman
*Attorney, Agent, or Firm*—Bacon & Thomas

[57] ABSTRACT

This invention relates to substituted 1,4-dihydropyridines showing interesting physiological activities, particularly on the cardiovascular system. 1,4-Dihydropyridines in accordance with the invention are substituted in the 4-position by a 2-chloropyrid-3-yl or a 2-methylthiopyrid-3-yl group, in the 3- and 5-positions by a methoxycarbonyl or ethoxycarbonyl group and in the 2- and 6-positions by a methyl group. Acid addition salts of these compounds are included in the present invention. The compounds can be prepared by reacting an appropriate 2-substituted nicotinaldehyde with an alkyl acetoacetate. Compounds in accordance with the invention have shown anti-hypertensive activity at very low doses.

7 Claims, No Drawings

4-(2-CHLORO- OR METHYLTHIOPYRID-3-yl)-3,5-DICARBALKOXY-2,6-DIMETHYL-1,4-DIHYDROPYRIDINE

This invention relates to substituted 1,4-dihydropyridines showing interesting physiological activities particularly on the cardiovascular system, and to processes for their preparation.

According to the present invention there are provided compounds of formula:

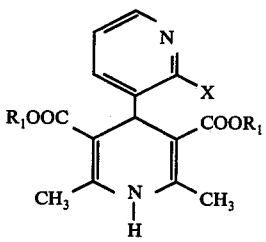
(I)

wherein X represents a chlorine atom, or a $CH_3S$ group, and $R_1$ represents a methyl or ethyl group, and acid addition salts thereof.

One particularly preferred compound of formula I, by virtue of its action on the cardiovascular system is 4-(2-chloropyrid-3-yl)-3,5-dicarbomethoxy-2,6-dimethyl-1,4-dihydropyridine, and its acid addition salts.

Compounds of formula I can be prepared by reacting an ortho-substituted aldehyde of formula:

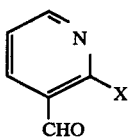
(II)

(wherein X is as hereinbefore defined) with an alkyl acetoacetate of formula $CH_3COCH_2COOR_1$ (wherein $R_1$ is as hereinbefore defined) preferably with two equivalents of the alkyl acetoacetate, and preferably in concentrated hydroalcoholic solution in the presence of an equivalent of ammonia.

Acid addition salts of compounds of formula I can be prepared by known methods.

Compounds of formula (II) can be prepared using a weak oxidising agent such as manganese dioxide or SARETT's reagent (pyridine-chromic anhydride complex) to oxidise a 3-hydroxymethyl 2-substituted pyridine of formula:

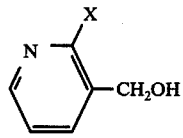
(III)

(wherein X is as hereinbefore defined) in an organic solvent such as chloroform, dichloromethane or the like.

The compounds of formula (III) can be prepared by reducing a 2-substituted nicotinic acid or a methyl or ethyl ester thereof using a conventional reducing agent such as lithium aluminium hydride or a potassium borohydride-lithium chloride mixture in an organic solvent such as ether or tetrahydrofuran.

While exhibiting very low acute and chronic toxicity levels, compounds in accordance with the invention have interesting physiological activities, and in particular an intense action on the cardiovascular system.

Indeed, compounds of formula I and their physiologically acceptable addition salts have been shown to exhibit a very considerable anti-hypertensive activity at very low doses. Haemodynamic properties of the compounds in accordance with the invention show a considerable increase of coronary flow per unit of work.

Compounds in accordance with the invention have been found to reduce peripheral and coronary vascular resistance, and to reduce the post-charge on the heart.

The present invention therefore provides pharmaceutical compositions comprising at least one compound of formula I (as hereinbefore defined) or a physiologically acceptable acid addition salt thereof, in association with a pharmaceutical carrier or excipient. Such compositions are preferably in dosage unit form.

In human therapy, compounds in accordance with the invention can be administered orally or parenterally. They can be used for example in the background treatment of angina pectoris or high blood pressure at a daily dose of 5 to 100 mg.

Compositions in accordance with the invention can be presented in the form of gels containing, for example, 20 mg and of injectable ampoules containing for example 10 mg, of a compound of formula I or a physiologically acceptable acid addition salt thereof.

In addition, compounds in accordance with the invention have been found to have particularly interesting therapeutic, i.e. activity/toxicity, ratios, and they have shown themselves to be particularly stable in terms of time and light.

The following Examples are given by way of illustration only:

EXAMPLE 1

4-(2-chloropyrid-3-yl)-3,5-dicarbethoxy-2,6-dimethyl-1,4-dihydropyridine

Formula I ($R_1$ = Et; X = Cl)

A solution of 15 g of 2-chloro-nicotinaldehyde, 15 ml of concentrated ammonia and 27.5 g of ethyl acetoacetate in 80 ml ethanol was refluxed for 8 hours.

The reaction mixture was then left for one night at room temperature.

The crystals which had formed were dried and carefully washed with isopropanol.

In this way 20 g of 4-(2-chloropyrid-3-yl)-3,5-dicarbethoxy -2,6-dimethyl-1,4-dihydropyridine were obtained in the form of very slightly yellow crystals (m.p. = 206°- 208° C).

EXAMPLE 2

4-(2-Chloropyrid-3-yl)-3,5-dicarbomethoxy-2,6-dimethyl-1,4-dihydropyridine

Formula I (X = Cl; $R_1$ = Me)

According to the method of Example 1, but using 14.5 g of 2-chloronicotinaldehyde and 23.8 g of methyl acetoacetate, 19.1 g of 4-(2-chloropyrid-3-yl)-3,5-dicarbomethoxy-2,6-dimethyl-1,4-dihydropyridine were obtained in the form of very slightly yellow crystals (m.p. = 262°-264° C).

EXAMPLE 3

3-Hydroxymethyl-2-methylthiopyridine

Formula III (X = S — CH$_3$)

14.9 g of lithium chloride were added in small amounts and with stirring, to a solution of 57.6 g of methyl 2-methylthionicotinate and 18.7 g of potassium borohydride in 600 ml tetrahydrofuran.

When the addition was complete, the reaction mixture was refluxed for 4 hours.

After cooling, ice and water were added to the reaction mixture, and the organic products were extracted with ether which was carefully washed with water and dried over sodium sulfate.

After evaporation of the ether, 45.5 g of 3-hydroxymethyl-2-methylthiopyridine were obtained in the form of white crystals (m.p. = 60° C).

EXAMPLE 4

2-Methylthionicotinaldehyde

Formula II (X = S — CH$_3$)

294 g of manganese doixide were added in small amounts with vigorous stirring to a solution of 45.5 g 3-hydroxymethyl-2-methylthiopyridine in 1 liter of cloroform. When the addition was complete, agitation was continued for 6 hours at room temperature, then the mixture was filtered through cellite.

Evaporation of the filtrate enabled 44.9 g 2-methylthionicotinaldehyde to be recovered in the form of white crystals (m.p. = 45° C).

EXAMPLE 5

4-(2-Methylthiopyrid-3-yl)-3,5-dicarbethoxy-2,6-dimethyl-1,4-dihydropyridine Formula I (R$_1$ = Et; X — SCH$_3$)

A solution of 10 g 2-methylthionicotinaldehyde, 7.85 ml of concentrated ammonia and 17 g of ethyl acetoacetate in 30 ml of ethanol was refluxed for 5 hours.

After cooling and adding water and ice, the reaction mixture was extracted with ether which was carefully washed with water and dried over sodium sulfate. After evaporation of the solvent, 16.5 g of crystals were obtained, which were recrystallised from a cyclohexane-ether mixture (9:1) to give 8.6 g of 4-(2-methylthiopyrid-3-yl)-3,5-dicarbethoxy-2,6-dimethyl-1,4-dihydropyridine in the form of white crystals (m.p. = 140° C).

EXAMPLE 6

This Example illustrates the haemodynamic cardiovascular properties of compounds in accordance with the invention.

Unsorted dogs, male or female, were anaesthesized with sodium mebubarbital (30 mg/kg intravenously) and artificially ventilated by means of a Pesty RPP pump (trade mark). They were oxygen-supplemented.

A measurement was taken of:

systolic carotidian pressure (P.Syst.) and diastolic pressure (P.diast.);
the heart rate (H.R.);
the ascendic aorta flow (A.Ao);
the circumflex aorta flow (C.Ao);

A calculation was made of:

the means blood pressure (mmHg) (P.mean) = Diastolic pressure + (0.43 × differential pressure);
the work of the left ventricle (kgm/min) (LVW) = aorta flow (1/min) × mean blood pressure (mmHg) × 13.5 × 1.055 × 10$^{-3}$;
the peripheral vascular resistance (mmHg/liter/min) (P.V.R.) = mean blood pressure (mmHg)/aorta flow (/min);
The systolic ejection volume (ml) (S.E.V.) = aorta flow (ml/min)/heart rate (beats/min.);
the coronary vascular resistance (mmHg/ml/min) (Co.V.R) = mean blood pressure (mmHg)/coronary flow (ml/min);
the coronary rate per beat (CoR/beat) = coronary rate (ml/min)/heart rate (Beats/min);
the coronary rate per left ventricle work unit (Co.R/LVWU) = coronary rate (ml/min)/left ventricle work (kgm/min).

The detected signals were amplified and recorded on a Beckman Dynograph (trade mark). The compounds under test were injected intravenously (saphene vein). Table I summarizes the percentage variations noted at the height of coronary vaso-dilation (Co.R) and of hypotension (B.P.) and the length of action of the compounds of Examples 1, 2, 5 and 6.

EXAMPLE 7

This Example illustrates anti-hypertensive action of compounds in accordance with the invention in rats with genetically high blood pressure.

The systolic blood pressure of the rats with genetically high blood pressure (Okamoto species), aged from 14 to 20 weeks, was measured by non-blood means at the level of the caudal artery by means of a PE 300 Narco Biosystem (trade mark) electrophygmograph.

The heart rate was calculated from the systolic blood pressure signals.

The animals were placed in a thermostated enclosure at 30° C, before each measurement.

Measurements were taken before, and then after the administration of the compounds of the various Examples. The products were administered intraperitoneally, suspended in water with Tween.

Table II below shows the variation in percentages of systolic blood pressure and of heart rate, obtained at different times after injection of the compounds under test relative to the first reference measurement.

TABLE I

| Ex. No. | No. of dogs | Dose (μg/kg) | | P.Syst. Δ % | P.Diast. Δ % | P.mean Δ % | H.R. Δ % | A.Ao Δ % | C.Ao Δ % |
|---|---|---|---|---|---|---|---|---|---|
| 1 | 5 | 5 | C.Ao | −10 ± 1.8 | −18 ± 0.9 | −14 ± 0.9 | 0 ± 1.8 | +17 ± 3.6 | +64 ± 12.4 |
|  |  |  | P.A. | −12 ± 2.3 | −32 ± 7.1 | −22 ± 4.1 | 0 ± 2.0 | +25 ± 6.8 | +39 ± 13.2 |
|  |  | 20 | C.Ao | −12 ± 4.1 | −21 ± 3.7 | −17 ± 4.0 | −4 ± 1.1 | +10 ± 3.5 | +87 ± 25.4 |
|  |  |  | P.A. | −20 ± 2.6 | −49 ± 6.4 | −34 ± 2.1 | −6 ± 1.4 | +28 ± 14.1 | +48 ± 30.7 |
| 2 | 3 | 5 | C.Ao. | − 5 ± 1.0 | −13 ± 1.8 | − 8 ± 0.7 | −1 ± 0.6 | + 2 ± 1.5 | +41 ± 5.2 |
|  |  |  | P.A. | − 8 ± 1.9 | −18 ± 0.9 | −13 ± 1.5 | +1 ± 0.7 | + 8 ± 2.1 | +26 ± 8.4 |

TABLE I-continued

| Ex. No. | No. of dogs | Dose | | | | | | | |
|---|---|---|---|---|---|---|---|---|---|
| | | 20 | C.Ao. | −12 ± 1.5 | −21 ± 2.1 | −16 ± 1.5 | −1 ± 0.7 | 0 ± 1.5 | +54 ± 3.6 |
| | | | P.A. | −20 ± 3.3 | −36 ± 2.7 | −28 ± 2.5 | +1 ± 0.7 | + 4 ± 1.9 | +18 ± 18.3 |
| | | 5 | C.Ao. | − 4 ± 0.6 | −19 ± 2.7 | −12 ± 0.9 | −2 ± 1.9 | +11 ± 1.2 | +51 ± 6.8 |
| 5 | 5 | | P.A. | − 1 ± 0.9 | −24 ± 5.8 | −12 ± 2.7 | +4 ± 1.3 | +30 ± 6.3 | +46 ± 14.0 |
| | | 20 | C.Ao. | −10 ± 1.5 | −31 ± 3.9 | −20 ± 2.2 | −6 ± 1.5 | + 4 ± 2.6 | +66 ± 4.4 |
| | | | P.A. | −10 ± 2.7 | −45 ± 3.6 | −27 ± 1.2 | −3 ± 1.6 | +29 ± 2.6 | +47 ± 10.0 |

| Ex. No. | No. of dogs | L.V.W. Δ % | P.V.R. Δ % | S.E.V. Δ % | Co.V.R. Δ% | Co.R/Beat Δ % | Co.R/LVWU Δ % | Duration of action (min) |
|---|---|---|---|---|---|---|---|---|
| 1 | 5 | 0 ± 4.2 | −26 ± 1.6 | +17 ± 3.9 | −46 ± 4.3 | +65 ± 15.0 | +65 ± 15.7 | 5 |
| | | −3 ± 8.8 | −37 ± 4.2 | +24 ± 5.7 | −43 ± 4.2 | +39 ± 14.0 | +47 ± 17.6 | |
| | | − 8 ± 2.3 | −24 ± 5.8 | +15 ± 3.7 | −51 ± 8.4 | +94 ± 27.2 | +106 ± 32.2 | 10 |
| | | −13 ± 9.7 | −40 ± 3.4 | +42 ± 11.1 | −49 ± 8.2 | +57 ± 32.0 | + 75 ± 37.5 | |
| | | − 7 ± 0.7 | −11 ± 1.8 | + 4 ± 0.9 | −35 ± 3.0 | +43 ± 4.6 | +51 ± 5.2 | 3 |
| 2 | 3 | − 6 ± 0.9 | −19 ± 2.9 | + 7 ± 1.5 | −30 ± 4.1 | +25 ± 8.6 | +33 ± 8.5 | |
| | | −16 ± 1.7 | −16 ± 2.4 | + 4 ± 1.9 | −46 ± 1.7 | +56 ± 3.2 | +84 ± 2.3 | 6 |
| | | −25 ± 3.5 | −30 ± 1.8 | + 3 ± 2.5 | −36 ± 9.3 | +17 ± 18.9 | +56 ± 17.7 | |
| | | − 2 ± 2.3 | −21 ± 0.4 | +13 ± 2.6 | −41 ± 2.2 | +54 ± 5.8 | +54 ± 4.7 | 4 |
| 5 | 5 | +14 ± 4.5 | −32 ± 4.4 | +25 ± 5.9 | −38 ± 5.2 | +40 ± 10.7 | +27 ± 7.7 | |
| | | −17 ± 8.1 | −23 ± 2.6 | +11 ± 2.9 | −52 ± 1.5 | +77 ± 5.4 | +101 ± 7.5 | 7 |
| | | − 6 ± 3.2 | −44 ± 0.6 | +33 ± 2.2 | −49 ± 2.9 | +51 ± 10.3 | + 55 ± 7.8 | |

TABLE II

| Ex. No. | Dose mg/kg IP | Percentage variation of systolic blood pressure | | | Percentage variation of heart rate | | |
|---|---|---|---|---|---|---|---|
| | | T + 30 min | T + 60 min | T + 24 h | T + 30 min | T + 60 min | T + 24 h |
| 1 | 0 | −10 ± 2.42 | − 8 ± 1.49 | −1 ± 2.08 | − 1 ± 3.86 | −1 ± 3.03 | 0 ± 2.89 |
| | 5 | −24 ± 3.92 | −13 ± 2.84 | −5 ± 2.39 | + 7 ± 5.35 | −1 ± 2.81 | +2 ± 3.05 |
| | 10 | −33 ± 2.75 | −20 ± 2.53 | −5 ± 2.23 | +12 ± 6.93 | +2 ± 4.23 | −1 ± 2.29 |
| | 20 | −37 ± 3.55 | −30 ± 1.98 | 0 ± 2.71 | +18 ± 4.59 | +15 ± 4.54 | +2 ± 1.96 |
| 2 | 20 | −25 ± 4.10 | −15 ± 2.91 | −7 ± 4.02 | − 7 ± 6.12 | −7 ± 6.12 | −10 ± 4.05 |
| | 0 | −12 ± 1.82 | − 5 ± 1.94 | −7 ± 3.07 | − 5 ± 1.82 | −3 ± 2.51 | −5 ± 2.27 |
| 5 | 5 | −20 ± 2.53 | −11 ± 1.99 | −11 ± 2.90 | + 3 ± 4.48 | −2 ± 3.76 | −3 ± 2.35 |
| | 10 | −34 ± 2.63 | −22 ± 2.80 | −6 ± 3.04 | +16 ± 3.71 | +3 ± 2.61 | −1 ± 1.87 |
| | 20 | −49 ±2.57 | −36 ± 2.96 | −7 ± 2.65 | +21 ± 3.21 | +15 ± 4.22 | −1 ± 2.22 |

We claim:

1. A compound of the formula

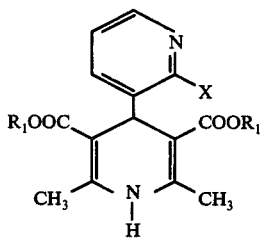

(I)

wherein X is selected from the group consisting of a chlorine atom and a CH$_3$S group, and each of the groups R$_1$ is the same and represents a methyl or ethyl group, or a physiologically acceptable acid addition salt thereof.

2. 4-(2-Chloropyrid-3-yl)-3,5-dicarbomethoxy-2,6-dimethyl-1,4-dihydropyridine or a physiologically acceptable acid addition salt thereof.

3. The compound of claim 1 which is 4-(2-chloropyrid-3-yl)-3,5-dicarbethoxy-2,6-dimethyl-1,4-dihydropyridine.

4. The compound of claim 1 which is 4-(2-methylthiopyrid-3-yl)-3,5-dicarbethoxy-2,6-dimethyl-1,4-dihydropyridine.

5. A pharmaceutical composition for the treatment of hypertension comprising an effective amount of a compound as claimed in claim 1 and a pharmaceutical carrier or excipient.

6. A composition as claimed in claim 5, in the form of dosage units.

7. A method for treating a human suffering from hypertension comprising administering orally or parenterally an effective amount of a compound as claimed in claim 1.

* * * * *